United States Patent [19]

L'Esperance, Jr.

[11] Patent Number: 4,773,414

[45] Date of Patent: * Sep. 27, 1988

[54] METHOD OF LASER-SCULPTURE OF THE OPTICALLY USED PORTION OF THE CORNEA

[75] Inventor: Francis A. L'Esperance, Jr., Englewood, N.J.

[73] Assignee: LRI L.P., New York, N.Y.

[*] Notice: The portion of the term of this patent subsequent to May 12, 2004 has been disclaimed.

[21] Appl. No.: 59,617

[22] Filed: Jun. 8, 1987

Related U.S. Application Data

[63] Continuation-in-part of Ser. No. 49,339, May 13, 1987, which is a continuation-in-part of Ser. No. 748,358, Jun. 24, 1985, Ser. No. 891,169, Jul. 31, 1986, and Ser. No. 891,285, Jul. 31, 1986, which is a continuation-in-part of Ser. No. 778,801, Sep. 23, 1985, abandoned, which is a continuation-in-part of Ser. No. 742,225, Jun. 6, 1985, abandoned, said Ser. No. 891,169, is a continuation-in-part of Ser. No. 780,335, Sep. 26, 1985, abandoned, which is a continuation-in-part of Ser. No. 740,276, Jun. 3, 1985, abandoned, said Ser. No. 748,358, Ser. No. 740,276, and Ser. No. 742,225, each is a continuation-in-part of Ser. No. 552,983, Nov. 17, 1983, abandoned.

[51] Int. Cl.$^4$ ............................................... A61F 9/00
[52] U.S. Cl. .................................. 128/303.1; 128/395
[58] Field of Search ................... 128/303.1, 362, 395, 128/397, 398

[56] References Cited

U.S. PATENT DOCUMENTS 4,665,913  5/1987  L'Esperance .................. 128/303.1
4,732,148  3/1988  L'Esperance .................. 128/303.1

Primary Examiner—William E. Kamm
Assistant Examiner—David Shay
Attorney, Agent, or Firm—Hopgood, Calimafde, Kalil, Blaustein & Judlowe

[57] ABSTRACT

The invention contemplates removal of epithelium-layer material from the anterior surface of the cornea, as a step preparatory to laser surgery, wherein controlled ultraviolet irradiation of the cornea is operative to surgically ablate corneal tissue within an epithelium-free area which is in the optically used central region of the cornea; the control is such (1) as first to effect essentially uniform-depth removal of Bowman's membrane to the extent of exposing only stroma tissue within said central region, and then (2) to so selectively distribute the ultraviolet radiation to then-exposed stroma tissue as to effect in stroma tissue a predetermined sculpted corrective-curvature change in the optically used region. Other important pre-surgury and post-surgery procedural steps are disclosed, for greater assurance of a predictable curvature change through the sculpting laser surgery.

7 Claims, 1 Drawing Sheet

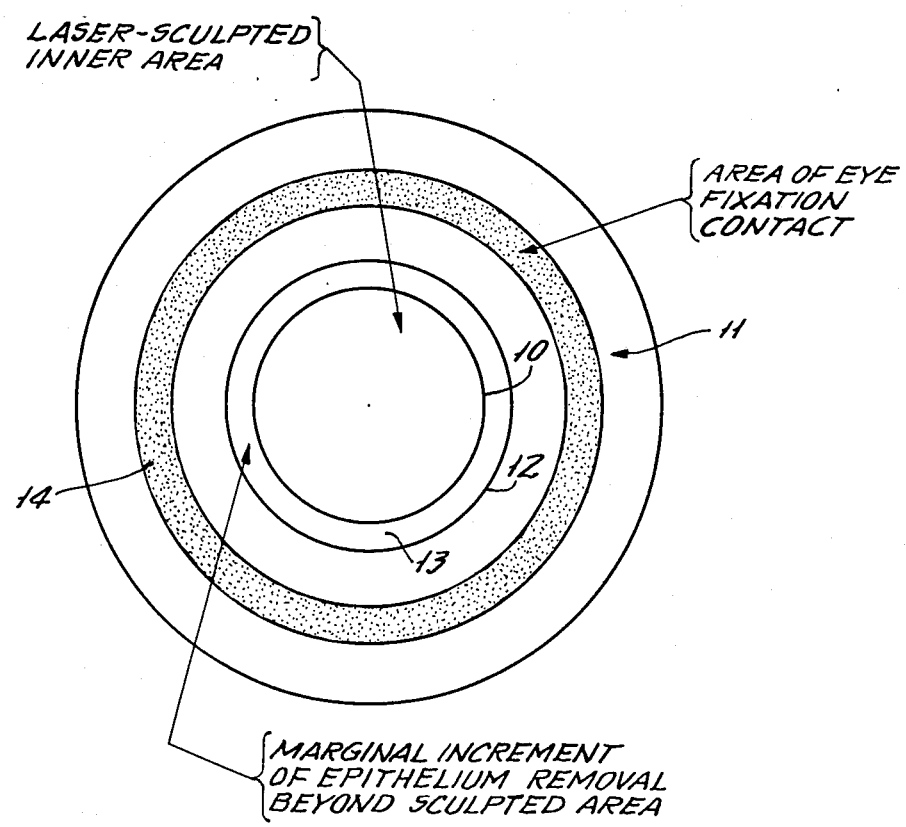

METHOD OF LASER-SCULPTURE OF THE OPTICALLY USED PORTION OF THE CORNEA

RELATED CASES

This application is a continuation-in-part of application Ser. No. 049,333, filed May 13, 1987; and said application Ser. No. 049,333 is a continuation-in-part of pending application Ser. Nos. 748,358, filed June 24, 1985, 891,169, filed July 31, 1986, and 891,285, filed July 31, 1986. Said application Ser. No. 748,358 is a continuation-in-part of original application Ser. No. 552,983, filed Nov. 17, 1983 (now abandoned). Said application Ser. No. 891,169 is a continuation-in-part of application Ser. No. 780,335, filed Sept. 26, 1985 (now abandoned); said application Ser. No. 780,335 is a continuation-in-part of application Ser. No. 740,276, filed June 3, 1985 (now abandoned); and said application Ser. No. 740,276 is a continuation of said original application. Said application Ser. No. 891,285 is a continuation-inpart of application Ser. No. 778,801, filed Sept. 23, 1985 (now abandoned); said application Ser. No. 778,801 is a continuation-in-part of application Ser. No. 742,225, filed June 6, 1985. (now abandoned); and said application Ser. No. 742, 225 is a continuation-in-part of said original application. The disclosures of said applications are incorporated herein by reference.

BACKGROUND OF THE INVENTION

The invention relates to that aspect of ophthalmic surgery which is concerned with operations upon the external surface of the cornea.

Operations of the character indicated include corneal transplants and keratotomies; such operations have traditionally required skilled manipulation of a cutting instrument. But, however keen the cutting edge, the mere entry of the edge into the surface of the cornea necessarily means a wedge-like lateral pressure against body cells displaced by the entry, on both sides of the entry. Such lateral pressure is damaging to several layers of cells on both sides of the entry, to the extent impairing the ability of the wound to heal, and resulting in the formation of scar tissue.

My original patent application Ser. No. 552,983, filed Nov. 17, 1983, includes a background discussion of the effects of various available wavelengths of laser radiation in ophthalmic surgery and, in particular, surgery performed on the anterior surface of the cornea. It is explained that radiation at ultraviolet wavelengths is desirable by reason of its high photon energy. This energy is greatly effective on impact with tissue, in that molecules of tissue are decomposed on photon impact, resulting in tissue ablation by photodecomposition. Molecules at the irradiated surface are broken into smaller volatile fragments without heating the remaining substrate; the mechanism of the ablation is photochemical, i.e., the direct breakdown of intra-molecular bonds. Photothermal and/or photocoagulation effects are neither characteristic nor observable in ablations at ultraviolet wavelengths, and cell damage adjacent the ablation is insignificant.

Said related-case applications deal with various concepts whereby laser radiation at ultraviolet wavelengths of 200-nm or less are controlled in delivery of laser radiation to the visually used area of the anterior surface of the cornea so as to penetrate the stroma and achieve a predeterminable volumetric removal of corneal tissue, thereby so correctively changing the profile of the anterior surface as to reduce a myopia, or a hyperopia, or an astigmatic abnormality which existed prior to such laser surgery.

Said related-case applications were concerned primarily with the methods and means of achieving desired corneal sculpture through controlled delivery of ultraviolet laser radiation. The disclosures of these applications were addressed to ophthalmic surgeons who presumably are skilled in tradational procedures; but, although the laser-sculpting procedures I disclosed were contrary to current professional practice and beliefs, in the sense that I called for ablation depths which necessarily involved traversing Bowman's membrane in order to penetrate the stroma, I have been surprised that those skilled in laser technology who would attempt to experimentally apply my disclosures to their own research, have been unduly preoccupied with the epithelium, namely, the thin regrowable layer which nature provides for protection of the anterior surface of the cornea. I have found that such preoccupation with the epithelium can not only produce an undesirable result but can also be a reason for unpredictability of a desired result.

BRIEF DESCRIPTION OF THE DRAWING

The FIGURE is a view of the anterior portion of a cornea with the varius operative areas indicated.

BRIEF STATEMENT OF THE INVENTION

It is an object of the invention to provide improved procedure, before performing sculpturing laser surgery of the character indicated, whereby the laser surgery per se may be performed on a patient's cornea with greater confidence and assurance of achieving a given prescribed optically improved result.

Another object is to perform curvature-correcting surgery on the anterior surface of the cornea by effecting the curvature-correcting profile essentially only in stroma tissue.

It is also an object of the invention to achieve the above result with improved post-operative procedure which favors smooth and sufficient epithelium regrowth over the surgically affected region of the cornea.

Still another object is to achieve the foregoing objects with procedural steps which are within existing skills of the ophthalmic surgeon and which use materials with which such surgeons are familiar.

The invention achieves these objects by performing the pre-operative step of removing the epithelial layer from a central area of the cornea, wherein such removed area is slightly greater than the area to be subjected to ablation under ultraviolet laser radiation, whereby such laser action is directed to an epithelium-free area, for immediate traversal of Bowman's membrane and penetration of the stroma; the traversal of Bowman's membrane is to essentially uniform depth so as to expose only stroma tissue within the ablated area, and then the ultraviolet radiation is so selectively delivered to the exposed stroma as to achieve a predetermined new curvature profile solely in stroma tissue. Precaution is taken to avoid deleterious dehydration effects in the thus-exposed area, and the laser-sculpting procedure is accomplished, generally to a maximum penetration depth of less than 40 microns, and within 30 to 40 seconds. Postoperative procedure favorable to smooth and efficient epithelial regrowth over the surgically sculptured region is also described.

DETAILED DESCRIPTION

The invention will be described in detail in connection with the accompanying drawing which, on an enlarged scale, is a schematic view in front elevation of the anterior aspect of the cornea, with markings to permit descriptive identification of different significant areas involved in use of the invention.

As generally indicated above, the invention is concerned with extra-operative procedural steps, i.e., beyond the particular ultraviolet-irradiation procedure relied upon to selectively ablate the anterior surface of the cornea, with penetration into the stroma, whereby to achieve such volumetric removal of corneal tissue as to correctively change an optically deficient pre-existing curvature to an optically improved new curvature. Illustrative description of such deficiencies and different techniques for their corrective improvement through selective irradiation from an ultraviolet laser, such as an argon-fluoride excimer laser, will be found in the above-noted pending patent applications and in those prior patent applications to which the pending applications bear a continuing or continuation-in-part relation; reference may therefore be had to said applications for detailed description.

Important to the method of the present invention is the procedural step wherein epithelial-layer material is so locally removed from the anterior surface of the cornea as to assure no ultraviolet irradiation of the epithelium. For such assurance, this procecdural step contemplates that epithelial-layer removal shall be throughout an area which continuously overlaps and surrounds the cornea-sculpting area of selective ablation via ultraviolet irradiation. If it is assumed that the cornea-sculpting area is a circle of 5 or 6-mm diameter, as could well be the case (a) for sphericalcurvature reduction (to reduce a myopia condition) or (b) for spherical-curvature increase (to reduce a hyperopia condition) or (c) for cylindrical-curvature reduction (to reduce an astigmatism condition), then the area of epithelial-layer removal should be a circle which fully laps the cornea-sculpting area, preferably with a circumferentially continuous margin of about 1-mm incremental radius outside the circle of cornea-sculpting ablation. In the drawing, the circle 10 of cornea-sculpting action is seen in the central optically used portion of a cornea 11, and a preferred circle 12 of epitheliallayer removal is seen to be concentric with circle 10, thus providing a margin 13 of incremental radius outside circle 10, whereby to assure against epithelium exposure to ultraviolet irradiation.

When the area of circle 12 is epithelium-free, Bowman's membrane tissue is externally exposed. This membrane is relatively thin and shell-like, in that it is of density which differs from that of underlying stroma. It is preferred to perform uniform ablation of Bowman's membrane before performing ablative sculpture and that such sculpture be performed substantially only on stroma tissue. The practiced eye of a skilled ophthalmic surgeon can visually recognize when and whether all of Bowman's membrane has been removed, in a first ablative step involving uniformly distributed ultraviolet irradiation within the epithelium-free area; generally, this will be to a penetrating depth of 10 to 15 microns. The exact depth to ablate Bowman's membrane and to expose only stroma tissue is not critical, as long as the surgeon can visually determine that essentially only stroma tissue is exposed, before initiating the second ablative step, namely, the selective distribution of ultraviolet radiation so as to accomplish ablative sculpture of a new curvature substantially only by selective volumetric removal of stroma tissue.

Preferred pre-operative (i.e., pre-surgery) procedural steps, in the illustrative context of circular areas delineated above and in the drawing, will appear from the following recital of specific steps and precautions which I have taken in laser-sculpting operation upon human patients to date:

1. With the patient lying on his back, with his head restrained to face straight up, and with retractors set to hold back upper and lower eyelids, a peri-bulbar or retrobulbar anesthetic is administered to obtain anesthesia of the anterior portion of the eye and relative akinesia of the extra-ocular muscles.

2. A suction device or other means for outer-annulus steadying contact with the eye is applied to an area 14 having substantial radial offset from the area 12 within which epithelium is to be removed.

3. Within the inner limit of the area 14 of eye-steadying contact, the epithelium is kept in normally moist condition, by application to the cornea of one or more drops of an isotonic solution.

4. Having selected a scraping tool, such as a molded plastic spatula-like implement having a relatively narrow blade, e.g., having a 2 to 3-mm wide scraping edge of moderate sharpness, proceed to dislodge only epithelial-layer material from within the circle 12, the dislodged material being pushed to and temporarily accumulated upon the remaining undisturbed epithelial layer, namely, within the annular area outside circle 12 and within the inner limit of the area 14 of fixation contact.

5. The scraping dislodgement of epithelium may or may not be totally effective with the indicated scraper, but if more moisture is needed to wash away all epithelial material within area 12, another drop f the isotonic solution can be applied, and a dry cotton-tipped tooth pick (e.g., a so-called "Q-Tip") may be employed to sweep area 12 clear of all epithelial material, thus exposing a clean and smooth anterior aspect of Bowman's membrane, within area 12. The same or another "Q-Tip" device is then used to pick up and discard all of the accumulation of scraped epithelial material, from the outer annulus, i.e., from the area around circle 12. At all stages of performing steps 4 and 5, extreme caution is needed to assure against any scratching or other mechanical invasion of Bowman's membrane.

6. The patient is now conditioned for one of the laser-sculpting procedures selected from said pending patent applications, it being understood that prior to any of the above-described pre-surgery steps, the laser-delivery surgical apparatus will have been brought to a condition of instant readiness to perform a predetermined control of ultraviolet irradiation within the laser-sculpting area 10. Generally speaking, the laser-sculpting operation begins immediately after completion of epithelium removal, and when the area of circle 12 is smoothly denuded and epithelium-free; as explained above, this is preferably a two-step procedure involving removal of Bowman's membrane tissue before performing laser sculpture essentially only on stroma tissue. Laser-sculpting proceeds to completion within one minute, and often less e.g., about 30 seconds for a two-diopter spherical change of curvature with a 5-mm diameter area; also generally speaking, the depth of penetration into the stroma will be less than 50 microns, e.g., about 20 microns for a two-diopter spherical change of curvature.

7. Immediately upon termination of the laser surgery of step 6 above, the speculum or other eye-contacting retainer means is removed, and a solution significantly containing a cycloplegic agent is applied, as by one or more drops of the solution, to the area of surgical operation, to temporarily paralyze ciliary and iris musculature, thereby preventing spasm, irritation or other patient discomfort; and an antibiotic ointment, such as an erythromycin or chloromycetin ointment is applied to environmentally protect and cover the entire exposed area of the cornea.

8. The lids are then released and taped in closed condition, and a moderate-pressure bandage is applied over the taped lids, the bandage being configured so as not to allow the lids to separate.

9. The patient is then given a quiescent post-operative recuperative period of rest, for enhanced opportunity of epithelium regrowth into smooth and total coverage of the anterior surface of the cornea. Generally speaking, this epithelium regrowth proceeds to substantial completion in about 48 hours. But bandage removal and replacement, at 11 to 12-hour post-surgery intervals, is recommended, in order to track the expected progress of epithelium regrowth. The patient is released upon the surgeon's judgment that epithelium regrowth is complete.

In my surgical experience to date, involving use of one or more inventions of above-identified patent applications, I have used special apparatus designed and constructed by Taunton Technologies Inc., of Monroe, Connecticut. Said special apparatus is the subject of pending patent applications, Ser. No. 938,633, filed Dec. 5, 1986 and Ser. No. 009,724, filed Feb. 2, 1987, as well as apparatus-divisional applications based on disclosures of one or more of the patent applications first identified above.

What is claimed is:

1. The method of changing the anterior surface of the cornea of an eye from an initial curvature in an optically used area having defective optical properties to a subsequent curvature having correctively improved properties within said optically used area, which method comprises:
    (a) removing only the epithelial layer from said area, whereby within said area Bowman's membrane is the externally exposed anterior surface of the cornea;
    (b) then directionally and uniformly within said area impacting said exposed surface with tissue-ablating laser irradiation to ablate the anterior surface of the cornea with volumetric removal of corneal tissue to a uniform depth which is at least the thickness of Bowman's membrane, whereby stroma tissue is directly exposed in said area; and
    (c) then directionally and selectively within said area impacting the exposed stroma with tissue-ablating laser irradiation to ablate stroma tissue with volumetric removal of stroma tissue to such penetration depth and profile as to characterize the anterior surface of the cornea with said subsequent curvature.

2. The method of improving optical properties of an eye by operating essentially only upon the optically used area of the anterior surface of the cornea of the eye, which method comprises:
    (a) first removing epithelial material to the extent rendering said area epithelium-free;
    (b) then directionally and uniformly within said area impacting said exposed surface with tissue-ablating laser irradiation to ablate the anterior surface of the cornea with volumetric removal of cornea tissue to a uniform depth which is at least the thickness of Bowman's membrane, whereby stroma tissue is directly exposed in said area; and
    (c) then directionally and selectively within said area impacting the exposed stroma with tissue-ablating laser irradiation to ablate stroma tissue with volumetric removal of stroma tissue to such penetration depth and profile as to characterize the anterior surface of the cornea with a predetermined corneal profile having improved optical properties.

3. The method of improving optical properties of an eye by operating essentially only upon the optically used area of the anterior surface of the cornea of the eye, which method comprises a two-step procedure of tissue-ablating laser radiation of the anterior surface of the cornea in a volumetric removal of corneal tissue and with depth penetration into the stroma and to a predetermined curvature profile, said first step being one of substantially uniformly distributed ablation to the extent of removing Bowman's membrane within said areea, whereby only stroma tissue is exposed within said area, and then selectively distributing the tissue-ablating laser irradiation to the exposed stroma tissue to achieve the predetermined curvature profile within said area.

4. The method of improving optical properties of an eye by operating essentially only upon the optically used area of the anterior surface of the cornea of the eye, which method comprises a two-step procedure of ultraviolet radiation and attendant ablative photodecomposition of the anterior surface of the cornea in a volumetirc removal of corneal tissue and with depth penetration into the stroma and to a predetermined curvature profile, said first step being one of substantially uniformly distributed ablative decomposition to the extent of removing Bowman's membrane within said area, whereby only stroma tissue is exposed within said area, and then selectively distributing the ultraviolet irradiation to the exposed stroma tissue to achieve the predetermined curvature profile within said area.

5. The method of improving optical properties of an eye by operating essentially only upon the optically used area of the anterior suface of the cornea of the eye, which method comprises:
    (a) first removing epithelial material to the extent rendering said area epithelium-free;
    (b) then directionally and uniformly within said area impacting said exposed surface with ultraviolet irradiation to ablate the anterior surface of the cornea by photodecomposition with volumetric removal of cornea tissue to a uniform depth which is at least the thickness of Bowman's membrane, whereby stroma tissue is directly exposed in said area; and
    (c) then directionally and within said area impacting the exposed stroma with ultraviolet irradiation to ablate stroma tissue by photodecomposition with volumetric removal of stroma tissue to such penetration depth and profile as to characterize the anterior surface of the cornea with a predetermined corneal profile having improved optical properties.

6. The method of changing the anterior surface of the cornea of an eye from an initial curvature in an optically used area having defective optical properties to a subsequent curvature having correctively improved properties within said optically used area, which method comprises:
   (a) removing only the epithelial layer from said area, whereby within said area Bowman's membrane is the externally exposed anterior surface of the cornea;
   (b) then directionally and uniformly within said area impacting said exposed surface with ultraviolet irradiation to ablate the anterior surface of the cornea by photodecomposition with volumetric removal of corneal tissue to a uniform depth which is at least the thickness of Bowman's membrane, whereby stroma tissue is directly exposed in said area; and
   (c) then directionally and within said area impacting the exposed stroma with ultraviolet irradiation to ablate stroma tissue by photodecomposition with volumetric removal of stroma tissue to such penetration depth and profile as to characterize the anterior surface of the cornea with said subsequent curvature.

7. The method of any one of claims 6, 5, 4, 1, 2 or 3, including the subsequent steps of applying an environmentally protective cover to said area and adjacent epithelium, and affording a quiescent post-operative period for epithelium regrowth over said area.

* * * * *

UNITED STATES PATENT AND TRADEMARK OFFICE
CERTIFICATE OF CORRECTION

PATENT NO. : 4,773,414

DATED : September 27, 1988

INVENTOR(S) : Francis A. L'Esperance, Jr.

It is certified that error appears in the above-identified patent and that said Letters Patent is hereby corrected as shown below:

On face of patent, at "[*] Notice:", the correct date on the second line should read -- May 19, 2004 --.

Col. 2    Line 27    Change "varius" to -- various --

Col. 3    Line 38    Change "sphericalcurvature" to -- spherical-curvature --.

Col. 3    Line 49    Change "epitheliallayer" to -- epithelial-layer --.

Col. 4    Line 40    Change "f" to -- of --.

Col. 6    Line 28    Change "areea" to -- area --.

Signed and Sealed this

Twenty-third Day of April, 1991

Attest:

HARRY F. MANBECK, JR.

Attesting Officer    Commissioner of Patents and Trademarks